Figure 1:
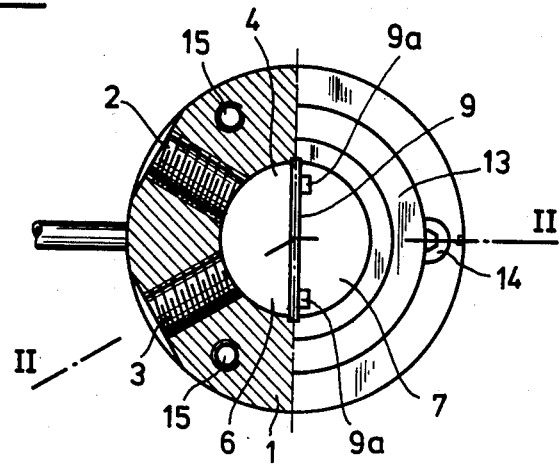

United States Patent [19]

Heimel et al.

[11] Patent Number: 4,674,884
[45] Date of Patent: Jun. 23, 1987

[54] CELL FOR A GAS ANALYZER

[75] Inventors: Helmut Heimel, Ronneburg; Albert Randow; Rudi Röss, both of Bruchköbel; Gerhard Wiegleb, Maintal, all of Fed. Rep. of Germany

[73] Assignee: Leybold-Heraeus GmbH, Cologne, Fed. Rep. of Germany

[21] Appl. No.: 640,311

[22] Filed: Aug. 13, 1984

[51] Int. Cl.⁴ ............................................. G01N 21/09
[52] U.S. Cl. ....................................... 356/440; 250/345
[58] Field of Search ............... 250/343, 344, 345, 373; 356/440, 246

[56] References Cited

U.S. PATENT DOCUMENTS

| 3,179,798 | 4/1965 | Savitzky | 250/343 |
| 3,727,050 | 4/1973 | Kerr | 250/343 |
| 3,854,050 | 12/1974 | Petersen et al. | 250/429 |
| 4,101,221 | 7/1978 | Schunck et al. | 250/343 |
| 4,175,233 | 11/1979 | De Palma et al. | 250/343 |
| 4,201,915 | 5/1980 | Schunk et al. | 250/343 |
| 4,395,632 | 7/1983 | Ross et al. | 250/343 |
| 4,436,428 | 3/1984 | Watanabe et al. | 250/345 |

FOREIGN PATENT DOCUMENTS

| 782938 | 5/1965 | Japan | 250/343 |
| 0792098 | 12/1980 | U.S.S.R. | 356/246 |

Primary Examiner—Carolyn E. Fields
Assistant Examiner—Richard Hanig
Attorney, Agent, or Firm—Felfe & Lynch

[57] ABSTRACT

Cell for gas analyzers, having a casing with a cylindrical bore which is divided by an axial wall of separation into two chambers. The one chamber serves for the gas being measured and the other for a reference medium. The chambers terminate in windows at both ends. To make such a cell resistant to pressure and corrosion, the reference medium is constituted by a transparent, glass-clear material which is disposed in the cylindrical bore. At each end of the cylindrical bore there is provided an annular shoulder for the support of an annular gasket and a window. The windows are held by annular compression flanges and annular gaskets.

1 Claim, 2 Drawing Figures

CELL FOR A GAS ANALYZER

BACKGROUND OF THE INVENTION

The invention relates to a cell for gas analyzers, having a casing with a cylindrical bore divided by an axial dividing wall into two chambers, the one being provided for the gas being measured and a measuring light beam, and the other for a reference medium and a reference light beam, and having windows on both sides, through which the measuring and reference light beams can pass.

A cell of this kind is disclosed by German publication DE-OS 30 10 516, and its use in a gas analyzer is described in DE-OS 27 20 636. A complete apparatus of this type is also disclosed in U.S. Pat. No. 4,101,221 - Schunck et al.

Whereas known cell is suitable for operating temperatures up to about 350° C., it is not, however, suitable for the analysis of corrosive gases at high pressures (e.g., 40 bar), and at a high temperature relative to these pressures (e.g. 150° C.).

In the known cell, only a reference gas is in the one chamber and only the gas being measured is in the other. Each chamber is provided with two connecting tubes, so that the known cell requires a total of four connections. The gas being measured unavoidably draws impurities into the one chamber, where some of them are precipitated and affect the transmission of the windows in the course of time. This simulates a change in the absorption of the gas being measured, which can lead to errors of measurement. Calibrating the analyzer before the measurement makes possible only a very limited compensation for this.

It is the object of the invention to improve a cell of the kind described above such that it can be used also at high pressures and for the analysis of corrosive gases at higher temperatures.

THE INVENTION

This object is achieved in the cell described above, in accordance with the invention, (a) by disposing in the cylindrical bore a semicylindrical body of a glass-clear, transparent material forming the reference medium, (b) by disposing at each end of the cylindrical bore annular shoulders for the support of a sealing ring and a cylindrical window, and (c) affixing the windows by means of annular compression flanges with annular gaskets.

By means of feature (a) it is brought about that it is no longer necessary to insert and seal into the cylindrical bore any special plane-parallel dividing wall that would have to be of stiff construction to resist high pressure on one side, with the necessity of devoting special care in manufacture to the sealing thereof. Instead, the partition wall is formed by the planar surface lying on the axis of the semicylinder, so that the entire semicylinder is exposed to the working pressure on all sides, so that neither special strength nor any kind of gasket are necessary. All that is necessary is to fix the semicylinder appropriately in the cylindrical bore, which can be done by means of simple holding elements of sheet metal. Neither is it necessary any longer to establish in the reference medium equality of pressure with the gas being measured, a thing which would be difficult to do in the case of great pressure fluctuations. Preferred materials for the semicylindrical body are silica, alumina, calcium fluoride, barium fluoride, lithium fluoride, or the like, depending on the particular application.

Feature (b) brings it about that, in contrast to the windows of German publication DE-OS 30 10 516, it is no longer necessary to use semicircular windows; instead, circular or cylindrical windows are used, which are substantially easier to seal against high internal pressures at high temperatures.

By means of feature (c) not only assembly but also maintenance and any repairs that might be necessary are substantially facilitated; after the removal of at least one of the two compression flanges, the cylindrical bore is easily accessible, and also the solid reference medium can easily be removed and, if necessary, cleaned along with the windows. The compression flanges permit uniform support of the windows against the relatively high internal pressures, so that high reliability and safety of operation are achieved. Moreover, forces originated by different thermal coefficients of expansion can easily be controlled in this manner.

At the same time, in accordance with the further invention, it is especially advantageous if between the semicircular end faces of the body (reference medium) and the circular windows a gap defined by plane-parallel walls is present for the entry of the gas being measured.

It has already been stated above that the (corrosive) gas being measured entrains impurities which precipitate in the cell. Accordingly, the precipitation forms both on the windows and on the semicircular end faces of the body (reference medium). Thus the inevitable smudging will occur not only on the measuring side but also on the reference side. On the reference side, on both sides of the two gaps, a total of four surfaces collect smudge, while on the measuring side only two such surfaces are present. The total of four surfaces on the reference side, however, takes into account the fact that the two gaps for the gas being measured are not as accessible, so that the smudging progresses more slowly in them. It is possible by selecting the gap width accordingly to match the flow conditions on the reference side, to those on the measuring side, so that the smudging conditions on the two sides will be approximately in balance. In this manner the length of time for which the cell can be operated until the next cleaning can be considerably extended.

Again, it is especially advantageous in accordance with the further invention for the compression flange to be provided with exhaust passages. If due to some leakage the corrosive gas being measured should escape from the cell, it cannot get into the corresponding measuring apparatus to cause serious damage therein, and instead it will be drawn away through the exhaust passages and returned to the circuit of the gas being measured. This is especially important when the gases are toxic gases which under no circumstances can be allowed to enter the atmosphere.

Figure 2:
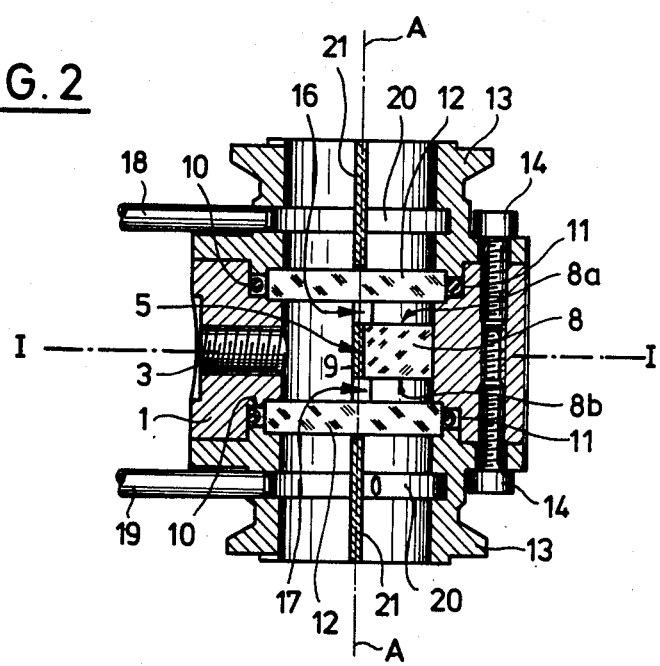

An embodiment of the invention will be explained below in conjunction with FIGS. 1 and 2, wherein:

FIG. 1 shows a radial cross section taken through a cell along the line I—I in FIG. 2, and FIG. 2 is an axial section taken through the cell of FIG. 1 along the line II—II.

FIG. 1 represents a casing 1 having a radial inlet bore 2 and a radial outlet bore 3. Both bores communicate with a central cylindrical bore 4, whose long axis A—A is identical with the casing axis.

The bore 4 is divided by an axial partition 5 into two chambers 6 and 7, of which chamber 6 is provided for the gas to be measured and the measuring light beam, and chamber 7 for the reference medium and a reference light beam. The reference medium is constituted by an approximately semicylindrical body 8 of silica, alumina, calcium fluoride, barium fluoride, lithium fluoride or the like, whose surface parallel to the axis A—A forms the wall of separation 5. The wall of separation 5 is aligned with the inlet and outlet bores 2 and 3 such that a mirror-image symmetrical relationship in accordance with FIG. 1 is the result. The body 8 has two approximately semicircular end faces 8a and 8b which are plane-parallel to one another. The body 8 is held in the bore 4 by a retaining plate 9 which sets the axial position of body 8 by means of tongues 9a, two of which are disposed above and two below the body 8.

At each end of the casing 1 there is an annular shoulder 10 for the accommodation of a sealing ring 11 and a cylindrical window 12, one above and the other below the body 8. The windows 12 are fixed in a mirror-image relationship by compression flanges 13 and annular gaskets 11. Due to the shape and size of the annular shoulders on the one hand and of the compression flange on the other, the gaskets 11 are compressed axially, so that they expand radially and come into hermetically sealing contact with the casing 1 and with the cylindrical surfaces of the windows 12. The windows themselves are not compressively stressed axially, since the compression flange comes in contact with the casing when the windows still have a slight axial clearance of, for example, 0.2 mm. On account of the arrangement selected, the windows 12 have a precise seat which is unaffected by any aging of the gaskets that might intervene. The compression flanges 13 are clamped to the casing 1 by three screws 14 distributed around the circumference, only the holes 15 for these screws being visible in FIG. 1.

It can also be seen in FIG. 2 that, between the semicircular end faces 8a and 8b of body 8 and the circular windows 12 there are gaps 16 and 17, respectively, defined by plane-parallel walls, and the gas circulating in and out of the bores 2 and 3 can enter these gaps.

FIG. 2 also indicates that the compression flanges 13 are provided with exhaust passages 18 and 19 through which any gases emerging at the windows can be drawn out. To this end grooves 20 are cut into the cylindrical inside surfaces of the compression flange 13. In the cylindrical bores of the compression flange 13 there are also outer dividing walls 21 which are flush with the dividing wall 5 of the body 8. In this manner an optical separation of the measuring light beam and reference light beam is assured along the entire length of the cell.

We claim:

1. A cell for gas analyzers, comprising:

A casing with a cylindrical bore which is divided by an axial wall of separation into two chambers, one of which is provided for the gas being measured and a measuring light beam, and the other for a reference medium and a reference light beam, and having windows at both ends for the entry of measuring and reference light beams, a solid semicylindrical body of a glass-clear transparent material forming the reference medium being disposed in said cylindrical bore in fixed geometrical relation to said chamber for the gas to be measured, annular gaskets, one being disposed at each end of said cylindrical bore, said casing having annular shoulder surfaces at the ends of said cylindrical bore for the support of one of said annular gaskets and of one of said windows at each end, and annular compression flanges holding fast said windows through said annular gaskets, said body having semicircular end faces, and a gap defined by plane-parallel walls for the entry of the gas being measured being present in each case between said semicircular end faces and said windows.

* * * * *